United States Patent [19]
Bockman et al.

[11] Patent Number: 5,556,645
[45] Date of Patent: Sep. 17, 1996

[54] METHODS OF ENHANCING WOUND HEALING AND TISSUE REPAIR

[76] Inventors: Richard Bockman, 180 E. 79th St., New York, N.Y. 10021; Peter Guidon, 1228 Biscayne Blvd., Union, N.J. 07083

[21] Appl. No.: 430,142

[22] Filed: Apr. 26, 1995

Related U.S. Application Data

[63] Continuation of Ser. No. 910,118, Sep. 14, 1992, abandoned, which is a continuation-in-part of Ser. No. 464,361, filed as PCT/US90/06606, Nov. 13, 1990 published as WO91/10437, Jul. 25, 1991, abandoned.

[51] Int. Cl.$^6$ .......................... A61K 33/24; A61K 31/28
[52] U.S. Cl. ............................................ 424/650; 514/492
[58] Field of Search ............................. 424/650; 514/492

[56] References Cited

U.S. PATENT DOCUMENTS

| | | | |
|---|---|---|---|
| 4,529,593 | 7/1985 | Warrell, Jr. et al. | 424/650 |
| 4,686,104 | 8/1987 | Bockman et al. | 424/650 |
| 4,704,277 | 11/1987 | Bockman et al. | 424/650 |
| 4,882,166 | 11/1989 | Graham et al. | 424/462 |

FOREIGN PATENT DOCUMENTS

| | | |
|---|---|---|
| 62230648A | 6/1987 | Japan . |

OTHER PUBLICATIONS

Bergkvist et al., "The Risk of Breast Cancer after Estrogen-Progestin Replacement", New England Journal of Medicine, 321:293–297 (1989).

Centrella et al., "Transforming Growth Factor β is a Bifunctional Regulator of Eplication and Collagen Synthesis in Osteoblast–enriched Cell Cultures from Fetal Rat Bone", The Journal of Biological Chemistry, 262:2869–2874 (1987).

Chirgwin et al., "Isolation of Biologically Active Ribunocleic nocleic Acid from Sources Enriched in Ribunuclease", Biochemistry, 18:5294–5299 (1979).

Ernst et al., "Estradiol Effects on Proliferation, Messenger Ribonucleic Acid for Collagen and Insulin–like Growth Factor–I, and Parathyroid Hormone–Stimulated Adenylate Cyclase Activity in Osteblastic Cells from Calvariae and Long Bones", Endocrin., 125:825–833 (1989).

Feinberg and Bogelstein, "A Technique for Radiolabeling DNA Restriction Endonuclease Fragments to High Specific Activity", Analytical Biochemistry, 132:6–13 (1983).

Jowsey et al., "Some Results of the Effects of Fluoride on Bone Tissue in Osteoporosis", J. Clin. Endocr., 28:869–874 (1968).

Kleeredoper et al., "Continuous Sodium Fluoride Therapy does not Reduce Vetebrae Fracture Rate in Postmenopusal Osteoporosis", J. Bone and Min. Res., 4:S376 1989).

Kream et al., "Characterization of the Effect of Insulin on Collagen Synthesis in Fetal Rat Bone", Ebdocrin., 116:296–302 (1985).

Lindsay et al., "Long–Term Prevention of Postmenopausal Osteoporosis by Oestrogen ", The Lancet, May 15, 1976, pp. 1038–1040.

Lowry et al., "The Quantitative Histochemistry of Brian", Journal of Biological Chemistry, 207:19–37 (1954).

Majeska et al., "Parathyroid Hormone–Responsive Clonal Cell Lines from Rat Osteosarcoma,a", Endocrin., 107:1494–1503 (1980).

Noda and Rodan, "Typeβ Trasforming Growth Factor (TGFβ) Regulation of Alkaline Phosphatase Espression and Other Phenotype–Related mRNAs in Osteoblastic Rat Osteosarcoma Cells", Journal of Cellular Physiology, 133:426–437 (1987).

Repo et al., "Effect of Gallium on Mineral Properties", Calcified Tissue International, 43:300–306 (1988).

Robery et al., "Osteoblasts Synthesize and Respind to Transforming Growth Factor–Type β (TGF–β) In Vitro", The Journal of Cellular Biology, 105:457–463 (1987).

Rodan and Martin, "Role of Osteoblasts in Hormonal control of Bone Resorption–A Hypothesis", Calcified Tissue International, 33:349–351 (1981).

Quarles et al., "Aluminum–Induced Mitogenesis in MC3T3–E1 Osteoblasts: Potential Mechanism Underlying Neoosteogenesis", Endocrinology 128:3144–3151 (1991).

Quarles et al. "Aluminum–induced neo–osteogenesis: a generalized process affecting trabecular networking in the axial skeleton", J. Bone and Mineral Res., 5:625–635 (1990).

Quarles et al., "Aluminum–induced de novo bone formation in the beagle. A parathyroid hormone–dependent event", J. Clinical Invest., 83:f1644–1650 (1989).

Quarles et al., "Induction of de novo bone formation in the beagle. A novel effect of aluminum", J. Clinical Invest., 81:1056–1066 (1988).

Seyedin et al., "Cartilage–inducing Factor–A Apparent Identity To Transforming Growth Factor–β", The Journal of Biological Chemistry, 261:5693+145 (1986).

(List continued on next page.)

*Primary Examiner*—Kevin E. Weddington
*Attorney, Agent, or Firm*—Brumbaugh, Graves, Donohue & Raymond

[57] ABSTRACT

Skin, connective and support tissue repair is enhanced and augmented by administering pharmaceutically acceptable gallium-containing compounds in amounts sufficient to provide therapeutic levels of elemental gallium. Gallium-containing compounds mimic the effects of endogenous growth factors to induce cells within these tissues to produce new matrix by increasing the formation of critical structural matrix proteins responsible for skin, support and connective tissue repair, maintenance and augmentation. Gallium-containing compounds are suitable for a variety of applications in wound healing, including dermatologic and cosmetic skin repair, bone fracture repair and successful bonding of implanted tissue grafts and connective and support tissue prostheses. The unique ability of the gallium-containing compounds to increase new matrix component formation and favorably alter the proliferation of specific cell types needed for tissue repair is separate and distinct from gallium's inhibitory activity on matrix-resorbing cells such as bone-resorbing osteoclasts.

10 Claims, No Drawings

OTHER PUBLICATIONS

Schenk et al., "Effect of Ethane-1-Hydroxy-1, 1-Diphosphonate (EHDP) and Dichloromethylene Diposphonate ($Cl_2MDP$) on the Calcification and Resorption of Cartilage and Bone in the Tibial Epiphysis and Metaphysis of Rats", Calcified Tissue Res., 11:196–214 (1973).

Sporn et al., "Some Recent Advances in the Chemistry and Biology of Transforming Growth Factor–Beta", The Journal of Cell Biology, 105:1039–1045 (1987).

ten Dijke and Iwata, "Growth Factors for Wound Healing", Bio/Technology, 7:793–798 (1989).

Warrell et al., "Gallium Nitrate Inhibits Calcium Resorption from Bone and is Effective Treatment for Cancer–Related Hypercalcemia", J. Clin. Invest., 73:1487–1490 (1984).

Warrell and Bockman, "Gallium in The Treatment of Hypercalcemia and Bone Metastasis" in Important Advances in Oncology 1989, J. B. Lippincott Co., New York, pp. 205–220 (1989).

Bockman et al., "Gallium Nitrate Stimulates Bone Collegen Synthesis", *Clincial Research*, 35:620 1987.

METHODS OF ENHANCING WOUND HEALING AND TISSUE REPAIR

This invention was made with United States Government support under grant NCI-CA38645 awarded by the National Institutes of Health. The Government has certain rights to the invention.

This application is a continuation of application Ser. No. 07/910,118, filed on Sep. 14, 1992, now abandoned; which is a continuation in part of Ser. No. 07/464,361, filed as PCT/US90/06606, Nov. 13, 1990 published as WO91/10437, Jul. 25, 1991 now abandoned.

FIELD OF THE INVENTION

The present invention relates to enhanced repair and augmentation of skin, connective and support tissues by gallium-containing compounds.

Prior U.S. Pat. Nos. 4,529,593 issued Jul. 16, 1985 to Warrell et al.; 4,686,104 issued Aug. 11, 1987 to Bockman et al. and 4,704,277 issued Nov. 3, 1987 to Bockman et al. describe methods of preventing excessive loss of calcium from human bone by the administration of pharmaceutically acceptable gallium-containing compounds. The ability of gallium-containing compounds to inhibit bone resorption (breakdown) prevents disordered calcium homeostasis.

Several agents including cisplatin, mithramycin, calcitonin and diphosphonates have been shown to inhibit bone resorption. Cisplatin and mithramycin are cytotoxic agents which when injected parenterally act by killing the cells responsible for tissue breakdown as well as those responsible for tissue formation. Calcitonin, a naturally produced hormone, transiently inhibits the activity of bone-resorbing cells (osteoclasts) to prevent bone breakdown. Calcitonin increases renal excretion of calcium and thus accelerates the loss of calcium from the body. Diphosphonates are a class of synthetic compounds that inhibit bone resorption. Etidronate (EHDP) is currently the only diphosphonate approved for use in the United States. None of the agents mentioned above have a proven beneficial effect on bone formation or wound healing; indeed, cisplatin and mithramycin are cytotoxic, and EHDP inhibits matrix-forming cells. Schenk et al., "Effect of Ethane 1-hydroxy-1,1-diphosphate (EHDP) and Dichloromethylene Diphosphonate ($Cl_2MDP$) on the Calcification and Resorption of Cartilage and Bone in the Tibial Epiphysis and Metaphysis of Rats", Calcif. Tis. Res., 11:196–214 (1973).

Fluoride-containing salts have been extensively tested for their effects on matrix-forming cells. Fluoride compounds are mitogenic—they cause the bone matrix-forming cells to proliferate and increase bone matrix formation. However, treatment with fluoride results in the production of a highly abnormal (woven-type) bone matrix structure. Such fluoride-induced bone is weaker than normal bone. Jowsey et al., "Some Results of the Effect of Fluoride on Bone Tissue in Osteoporosis", J. Clin. Endocrinol., 28:869–874 (1968). Indeed, a recently completed study showed fluoride did not significantly reduce the prevalence of skeletal fractures in osteoporotic women. Kleerekoper et al., "Continuous Sodium Fluoride Therapy Does Not Reduce Vertebral Fracture Rate in Postmenopausal Osteoporosis", J Bone and Min. Res., 4:S376 (1989)

Estrogens increase bone mass in estrogen-deficient, postmenopausal women. Lindsay et al, "Long-Term Prevention of Postmenopausal Osteoporosis by Estrogen Treatment", Lancet, 1:1038–1041 (1976). Estrogen directly affects bone-forming cells to increase matrix elements such as collagen and to increase an endogenous growth factor, insulin-like growth factor-I. Ernst et al., "Estradiol Effects on Proliferation, Messenger RNA for Collagen and Insulin-like Growth Factor-I, and Parathyroid Hormone-Stimulated Adenylate Cyclase Activity on Osteoblastic Cells from Calvariae and Long Bones", Endocrinol., 25:825–833 (1989). However, the benefits of estrogen treatment are limited to perimenopausal women. Furthermore, estrogen treatment is associated with increased risk of uterine and breast cancer. Bergkvist et al., "The Risk of Breast Cancer After Estrogen and Estrogen-Progestin Replacement", N. E. J. Med., 321:293–297 (1989).

Recently, naturally produced substances have been discovered which promote growth and healing of connective and support tissues. Such substances have been termed growth factors. Growth factors, usually proteins, initiate programs of differentiation and/or development within an organism.

Although growth factors would appear to be ideal for inducing support and connective tissue repair, such factors are not practically useful as pharmaceutical agents. Growth factors are not stable and tend to break down upon storage. As proteins, growth factors are not suitable for oral administration since they are digested and destroyed before entering the blood stream. Since they are only slowly absorbed by the body and rapidly broken down, growth factors cannot be satisfactorily administered as topical ointments. As a result of the lability of growth factors the preferred route of administration is parenteral thus requiring medically supervised administration. Unfortunately, many of the growth factors are species specific and are recognized as foreign by other species. Thus, there is the constant danger of eliciting an immune response. Lastly, there is no evidence that growth factors when administered parenterally, target to skin, connective and support tissues.

With the exception of certain recently described naturally occurring factors, there is no disclosure or suggestion in the prior art of a pharmaceutically acceptable compound that can induce skin, connective and support tissues to synthesize new matrix components in a manner that simulates natural conditions of growth, healing and repair. Additionally, there are no reports of pharmaceutically acceptable compounds that normalize the function of matrix forming cells and results in the production of new, normal skin, connective and support tissue components that enhance tissue repair and augmentation.

SUMMARY OF THE INVENTION

The present invention is a method of enhancing skin, connective and support tissue repair and augmentation by administering to a subject with a wound, tear or break, or deficiency of matrix components in skin, connective and support tissues, a pharmaceutically acceptable gallium-containing compound in an amount sufficient to increase the selective synthesis of matrix components so as to enhance repair or augment the strength and appearance of the skin, connective and support tissues.

DETAILED DESCRIPTION OF THE INVENTION

It has now been found that pharmaceutically acceptable gallium-containing compounds such as gallium nitrate mimic the molecular action of transforming growth factor-$\beta$ (TGF-$\beta$) with respect to inducing the synthesis of both mRNA and proteins involved in wound healing. In particular, results have been obtained with gallium nitrate treated skin and bone cells indicating that the mechanism of action of gallium is similar to that of TGF-β in wound healing.

Mechanisms of wound healing are similar for skin, connective and support tissues. The tissues being discussed include not only skin, bone, cartilage and tendon but also those tissues containing a supporting fascia made up of collagen matrix that encapsulate muscles and organs. Although wound healing requires a complex series of events that are not well defined, it is known that growth factors are required. Such factors are released into the wounded area, on migrate into the wound, there the factors stimulate growth of keratinocytes and fibroblasts, initiate angiogenesis and stimulate matrix formation and remodeling of the wounded area. ten Dijke et al., "Growth Factors for Wound Healing", Bio/Technology, 7:793–798 (1989).

From the data presented below it is evident that gallium-containing compounds mimic the action of TGF-β by directly stimulating the activity of matrix-forming cells and consequently enhancing the formation of matrix components. Matrix-forming cells synthesizing the structural elements of connective and support tissues respond to gallium-containing compounds in a manner similar to that of TGF-β, the growth-factor-like effects of these compounds enhance the repair or augment the strength of skin, connective and support tissues. The mechanisms of wound healing are similar in many respects for man and animals; hence veterinary applications of this invention are also apparent.

Bone, a typical example of a connective and support tissue, provides an ideal model system in which the mechanisms of wound healing can be examined in detail. Bone has been studied extensively and is easily manipulated. Bone is formed by matrix-producing cells known as osteoblasts. Osteoblasts are derived from local mesenchymal (stromal) precursors which differentiate into osteoblasts. The bone-forming osteoblasts produce two types of matrix. The first is an organic matrix made predominantly from the structural protein collagen, the second is a mineral matrix made up of calcium and phosphate found almost exclusively as hydroxyapatite in the form of fine crystalline particles distributed selectively along the collagen fibers. It is the organic collagen matrix and the orientation of the proteins in that matrix that determine the architectural and structural integrity of bone. The normal lamellar pattern of the collagen fibrils provides the tensile strength of bone.

New collagen synthesis is a necessary prerequisite for skin, support and connective tissue repair and augmentation. In bone, collagen synthesis is required for fracture repair, the successful bonding of grafts and prosthetic devices and to increase bone mass and strength. Several non-collagen molecules synthesized by the osteoblast including osteonectin, osteopontin and osteocalcin are thought to be necessary for ordered bone matrix formation. It is the mineral matrix that provides the stiffness and compressive strength of bone. The osteoblast is responsible for producing both the organic and mineral matrices as well as regulating the rate of formation and the architecture of newly formed bone. Further, the osteoblast, through its production of signal molecules, regulates the activity of the bone-dissolving cells, osteoclasts. The osteoblast is therefore the pivotal cell in the regulation of bone formation. Rodan et al., "Role of Osteoblasts in Control of Bone Resorption", Calcif. Tis. Int., 33:349–351 (1981). In addition to the proteins used in the synthesis of the organic matrix, the osteoblast produces specific enzymes. One such enzyme, bone alkaline phosphatase, has been used as a reliable indicator for the normal activity of the osteoblast.

A second major class of bone cells, osteoclasts, are derived from unique precursors in the bone marrow. Osteoclasts are able to dissolve both the mineral and organic matrices of bone. Under normal conditions the actions of osteoblasts and osteoclasts are "coupled" such that osteoclasts model or remodel bone synthesized by osteoblasts into a structure best designed to provide support to the body. In certain pathologic conditions, osteoclast-mediated resorption of bone far exceeds bone formation. Accelerated osteoclastic activity leads to excessive release of calcium from bone and a concomitant net loss of skeletal mass, often with an attendant disturbance in calcium homeostasis in the form of elevated blood levels of calcium.

Bone formation by osteoblasts is a complicated process that is not fully understood. Recent studies have provided important new information about the molecular events leading to normal bone formation. In particular, growth factors have been identified within bone that elicit a specific pattern of protein synthetic activity by osteoblasts resulting in enhanced bone formation. One such factor, TGF-β, is known to be contained and produced within bone. Seyedin et al., "Cartilage-inducing Factor", J. Biol. Chem., 261:5693–5695 (1986); and Robey et al., "Factor-Type β (TGF-β) in vitro", J. Cell Biol., 105:457–463 (1987). TGF-β can stimulate expression of the genes in osteoblasts that lead to synthesis of proteins responsible for new bone formation. Centrella et al., "Transforming Growth Factor-β is a Bifunctional Regulator of Replication and Collagen Synthesis in Osteoblast-enriched Cell Cultures From Fetal Rat Bone", J. Biol. Chem., 262:2869–2874 (1987); and Noda et al., "Type Beta Transforming Growth Factor Regulation of Alkaline Phosphatase Expression and Other Phenotype-related mRNA's in Osteoblastic Rat Osteosarcoma Cells", J. Physiol., 133:426–437 (1987). Coincidentally, TGF-β decreases the synthesis of specific proteases and signal proteins (such as osteocalcin) that normally are associated with the break down of matrix proteins. Sporn et al., "Some Recent Advances in the Chemistry and Biology of Transforming Growth Factor-β", J. Cell Biol., 105:1039–1045 (1987). These coordinate activities induced by TGF-β promote the accumulation of matrix elements explain the improved wound healing seen in TGF-β treated animals. Sporn et al. ibid. Agents mimicking the actions of naturally occurring growth factors such as TGF-β are expected to have a favorable effect on wound healing in general, and bone formation and skin and bone healing in particular.

Gallium nitrate has been shown to be effective in blocking osteoclastic bone resorption in patients with cancer and in preventing excessive loss of calcium from bone by inhibiting osteoclastic resorption. Warrell et al., "Gallium Nitrate Inhibits Calcium Resorption from Bone and is Effective Treatment for Cancer Related Hypercalcemia", J. Clin. Invest., 73:1487–1490 (1984); Warrell and Bockman, U.S. Pat. No. 4,529,593; and Bockman and Warrell, U.S. Pat. Nos. 4,686,104 and 4,704,277. However, unlike the related chemotherapeutic agents cisplatin or mithramycin, gallium nitrate inhibits resorption without being cytotoxic to osteoclasts. Rather, it appears to subtly alter the biochemical function of osteoclasts, rendering them less able to dissolve the bone matrices. While preventing bone dissolution may preserve existing skeletal mass, it is not as beneficial as increasing bone formation, especially when skeletal mass is already inadequate and at risk to fracture or tear. New bone matrix formation is essential to heal existing fractures, increase bone mass and to maintain bone grafts and prosthetic devices that are placed in bone to augment bone strength and function.

Since the original observations of the anti-resorptive activity of gallium, additional studies have been undertaken to determine the effects of gallium-containing compounds on osteoblast function with regard to bone formation. It has now been found that gallium-containing compounds induce osteoblastic cells to synthesize bone matrix components in a manner that mimics the action of naturally occurring bone-growth factors. This effect is specific for gallium-containing compounds and not other metals, near metals or antiresorptive compounds. In fact, two metals (zinc chloride and ferrous chloride) appear to increase the levels of proteins associated with bone resorption.

Wound healing involving skin is an example of tissue repair. One aspect of wound healing in skin involves the production of critical matrix components that form the architectural and structural lattice of skin. The major matrix component is type I collagen, similar to the case in bone. In the skin, it is the fibroblast that synthesizes and releases new collagen into the wound site. Unlike bone, this matrix is not mineralized. Other proteins produced by fibroblasts contribute to the matrix. One such protein, fibronectin, is thought to function as an important anchoring protein, helping to bind key cells to the underlying matrix. Fibronectin, the synthesis of which is enhanced during wound repair, is also produced by fibroblasts.

In skin and bone, the effects of gallium-containing compounds mimic the effects of TGF-$\beta$, a factor known to be involved in wound healing of skin, support and connective tissues throughout the body. Gallium-containing compounds are thus useful in enhancing bone healing, skin healing and the healing of other connective and support tissues as well as augmenting their mass by the synthesis of proteins associated with wound healing even in the absence of a specific wound. Gallium-containing compounds, by virtue of their ability to mimic natural growth factors found in bone, are suitable for use in inducing the formation of skin, connective tissue matrix elements and thus to augment the strength of all connective and support tissues as well as to repair specific injuries (wounds) to such tissues.

A further advantage of the present invention is that gallium-containing compounds can be applied to the site of injury. In some cases, gallium shows a preference to accumulate in specific connective tissue, such as skin and bone, offering the advantage that the agent can target to tissues in which it has beneficial effects. Previous teachings suggested that gallium-containing compounds had to be administered parenterally, thus necessitating hospitalization and the administration of relatively high concentrations of gallium. According to the present invention, gallium-containing compounds can now be applied directly to the site of injury or to the region requiring augmentation, resulting in lower serum, organ and non-involved tissue levels of gallium with increased effectiveness at the site of injury, and a concomitant decrease in the risk of side effects. Thus the preferred method of application is topical.

The effective amount and method of administration of the particular gallium formulation may vary based on the nature of the condition and disorder being treated, its severity, the age of the patient and other factors evident to one skilled in the art. In general, gallium-containing compounds are pharmaceutically acceptable due to their low toxicity in the therapeutic dosage range, stability and ability to be incorporated into a wide variety of vehicles for numerous routes of administration.

Gallium-containing compounds are useful in the art of tissue implants. Tissue implants include but are not limited to bone grafts, cartilage grafts, tendon grafts, skin grafts and bone prostheses. The grafts can be selectively coated with topical applications containing gallium-containing compounds or impregnated by soaking or immersion in solutions of gallium-containing compounds prior to their implantation.

In bone, gallium-containing compounds not only enhance repair of fractures and tears and promote bone growth so as to facilitate incorporation of implants such as bone grafts and prosthetic devices but also enhance new formation of bone matrix in individuals with decreased skeletal mass so as to prevent fractures, breaks and tears. In other connective and support tissues, gallium-containing compounds enhance tissue formation so as to promote wound healing and facilitate incorporation of grafts such as tendon, cartilage and skin.

In skin, topical or subcutaneous administration of gallium-containing compounds enhances new skin matrix synthesis. Increased production of the connective matrix components would facilitate healing of tears, breaks or defects in skin. Increased matrix synthesis would increase skin thickness, thereby removing wrinkles due to aging. Gallium induced matrix synthesis could be used to selectively fill skin defects due to prior injury as from acne or previous trauma. Thus in addition to the uses in wound repair, gallium compounds could have many dermatologic and cosmetic uses for the treatment of skin disorders.

Gallium-containing compounds, especially gallium nitrate, in a pharmaceutically acceptable form and at doses far below those known to be cytotoxic have now been found to exert beneficial effects on osteoblasts, fibroblasts and keratinocytes. In explanted tissues, treatment with gallium nitrate has been found to enhance the synthesis of new connective and support tissue matrix elements. In intact animals, gallium nitrate treatment increases the incorporation of new calcium into bone. Gallium nitrate normalizes osteoblast function in living rats with an induced abnormality in bone formation.

According to the present invention, in order to obtain the beneficial effects of gallium, pharmaceutically acceptable gallium-containing compounds are administered to the patient in an amount sufficient to provide therapeutic levels of elemental gallium. Typically in the case of wound healing, therapeutic levels are attained when elemental gallium is present in a steady state concentration in blood of about 1–150 µM with a preferred range of about 1–50 µM or when elemental gallium is present in tissues at a steady state concentration of about 1–1000 ng/mg dry weight of tissue with a preferred range of about 1–500 ng/mg dry weight of tissue. However, if gallium-containing compounds are applied proximate to the site of injury, lower levels of gallium may be maintained within the body. For instance the effective level of gallium needed at the site of injury would be about 0.25–100 µM thereby resulting in limited levels of gallium in the blood and viscera since absorption from the site would be relatively insignificant. Administration of gallium-containing compounds would cease once wound healing has occurred. In the case of skin augmentation, lower concentrations of gallium-containing compounds are necessary and administration can be continuous for instance as a face cream applied daily.

Gallium-containing compounds are useful in formulating a variety of routes of administration. The route(s) of administration useful in a particular application are apparent to one of skill in the art. Routes of administration include but are not limited to topical, transdermal, parenteral, gastrointestinal, transbronchial and transalveolar.

Formulations of gallium-containing compounds suitable to be applied topically include but are not limited to implants, ointments, creams, rinses and gels. Formulations suitable for transdermal administration include but are not limited to suspensions, oils, creams and ointments applied directly or attached to a protective carrier such as a patch. Formulations suitable for parenteral administration include but are not limited to sterile solutions for intravenous, intramuscular, intraarticular or subcutaneous injection or infusion. Formulations suitable for gastrointestinal administration include, but are not limited to, pills or liquids for ingesting and suppositories for rectal administration. Formulations suitable for transbronchial and transalveolar administration include, but are not limited to various types of aerosols for inhalation. The above-mentioned formulations are meant to describe but not limit the methods of administering gallium-containing compounds. The methods of making the various formulations are within the ability of one skilled in the art and will not be described in detail here.

In bone and skin, gallium-containing compounds are indicated for use in treatment of tears, breaks, fractures, implants and inadequate connective tissue mass.

Gallium-containing compounds are suitable for treatment of all bone fractures, breaks and tears and are especially suitable for treatment of bone fractures that exhibit delayed healing and repair as a consequence of inadequate bone formation at the site of injury. In order to achieve enhanced healing of bone, gallium containing compounds can be administered by applying the gallium-containing compound to the affected area either in a topical ointment, rinse or gel or by placement of an implant impregnated with a gallium-containing compound proximate to the site of injury. Alternatively, suitable levels of a gallium-containing compound can be provided systemically for instance by parenteral, gastrointestinal, transbronchial or transalveolar administration.

Inadequate skeletal mass is defined as a loss of skeletal mass sufficient to place the individual at risk of skeletal failure such that fractures can result from the minimal trauma of everyday life. Such fractures cause significant morbidity, inasmuch as there is insufficient healing of the fractures. Gallium-containing compounds prevent such fractures by restoring diminished skeletal mass and promote healing of fractures that occur as a result of reduced skeletal mass. In treatment of patients with inadequate skeletal mass at increased risk of bone tears, breaks or fractures, preferred routes of administration include parenteral and gastrointestinal although transbronchial or transalveolar administration routes are also suitable. In treatment of such patients who have suffered a tear, break or fracture the methods of administration would be the same as those of other patients with tears, breaks or fractures.

Gallium-containing compounds are also suitable for use in the field of bone implants. Bone implants include both bone grafts and prosthetic devices. Implants are routinely used to replace damaged or diseased joints and to support or replace weakened or lost bone. Grafts restore bone mass and promote fracture healing while prosthetic devices restore mechanical strength and function to the skeletal system. Successful implantation and function of these devices depends on bonding of the adjacent bone to the implant. Such bonding requires new bone formation at the interface between the implant and the bone and proximate to the implant. Gallium-containing compounds enhance attachment, fixation and stabilization of implants by promoting new bone formation from the bone onto the implant. Additionally, gallium-containing compounds can enhance bone growth onto specific sites of the implant.

An estimated 10% of bone and joint prosthetic devices fail to function due to non-bonding of the bone to the implant. The resulting disability often requires reoperation and reimplantation. Gallium-containing compounds for enhancing new bone formation proximate to an implant may De administered topically at the implantation site. Gallium-containing compounds can also be incorporated into a coating on the surface of the prosthetic device. Such coatings may be composed of a polymer that allows slow diffusion of the gallium-containing compounds at a rate sufficient to enhance bone growth for a suitable period of time. Suitable polymeric coatings include, but are not limited to, hydroxyapatite, methacrylate and tricalcium phosphate. In order to enhance bone growth onto specific sites within the prosthetic device, the polymeric coatings can be applied only to the sites where boney in-growth is desired. Bone grafts can be coated with or soaked or immersed in a rinse or gel prior to implantation so as to impregnate the graft with the gallium containing compound.

For enhancing integration of bone and joint implants, gallium-containing compounds can also be administered parenterally, gastrointestinally, transbronchially or transalveolarly.

Gallium-containing compounds are suitable for the treatment of wound healing involving the skin. Gallium compounds are useful in dermatologic conditions that involve the skin. In either circumstance, gallium-containing compounds are capable of inducing new skin matrix synthesis thereby accelerating healing. In addition to the benefits during wound repair; gallium induced matrix augmentation in the skin can have beneficial cosmetic effects as in the repair of skin defects due to the loss of dermal elements necessary for maintaining tissue fullness and smoothness.

Gallium-containing compounds are useful in the treatment of wounds in connective and support tissue other than bone. Such tissue includes cartilage, tendon, collagen containing tissues that encapsulate organs and fascia. Collagen containing tissues that encapsulate organs include but are not limited to the renal and liver capsules, the meninges, the pericardium and the pleura. The so-called soft tissues of skin, muscle and organs are supported by a collagen containing connective tissue known as fascia, and it is the fascia that is essential for the structural integrity and wound healing of these tissues.

In treatment of injury to connective and support tissue, administration of gallium-containing compounds proximate to the wound is preferred. For instance, cuts, abrasions and burns can be topically coated with ointments, creams, rinses or gels, or by the use of transdermal patches or by subcutaneous administration. In treatment of injuries to skin, tendon, cartilage and collagen containing tissues that encapsulate organs, topical application of gallium-containing compounds is preferred, and the preferred routes of administration are topical and transdermal. Adequate levels of gallium can also be obtained by systemic administration such as parenteral, gastrointestinal, transbronchial or transalveolar.

Additionally, tendon, cartilage, fascia and skin grafts are commonly used to treat torn or damaged tissue. These grafts can be coated with, soaked or immersed, in rinses or gels containing gallium-containing compounds prior to implantation. Topical administration of gallium-containing compounds is also useful to promote healing of tendon, cartilage and skin grafts. As with bone implants, the gallium-containing compounds induce matrix component synthesis to enhance attachment, fixation and stabilization of implants by promoting new tissue growth onto the implant.

It has previously been shown that the active ingredient in gallium-containing compounds is the elemental gallium itself and not any accompanying salt. Therefore any compound which provides adequate blood and tissue levels or tissue levels proximate to the site of injury of elemental gallium can be used according to the present invention. Gallium nitrate has been used in the following examples and is representative of all pharmaceutically acceptable gallium-containing compounds capable of providing therapeutically effective levels of elemental gallium for uptake by the patient. Use of the term "gallium-containing compound" denotes one or more pharmaceutically acceptable compounds capable of supplying therapeutic levels of elemental gallium. Such compounds include but are not limited to gallium nitrate, gallium phosphate, gallium citrate, gallium chloride, gallium fluoride, gallium carbonate, gallium formate, gallium acetate, gallium tartrate, gallium maltol, gallium oxalate, gallium oxide, and hydrated gallium oxide. Coordination complexes of gallium including but not limited to gallium pyrones (such as those derived from kojic acid); gallium pyridones (such as desferal); gallium hydroxymates; gallium aminocarboxylates or gallium oximes (such as 8-hydroxy quinolone) are also included in the present invention. Gallium bound to proteins such as but not limited to transferrin or lactoferrin illustrates another class of gallium-containing compounds that are included in the present invention. Gallium is bound to proteins by means known in the art.

The present invention is further illustrated by the following specific examples, which are not intended in any way to limit the scope of the invention.

EXAMPLE 1

The Effects of Gallium-Containing Compounds on Messenger RNA Levels in Human Fibroblast and Rat Osteoblast Cell Lines The cell lines used in this study include human skin fibroblasts and a rat osteogenic sarcoma tumor cell line (ROS 17/2.8). The fibroblasts are primary cultures derived from human skin. The rat osteosarcoma cell line is a permanent cell line that maintains many of the characteristics of osteoblasts. Majeska et al., "Parathyroid Hormone: Responsive Clonal Cell Lines from Rat Osteosarcoma", Endocrinol., 107:1494–1503 (1980). To ascertain the specificity of gallium-containing compounds, and compare the compounds to TGF-$\beta$, the cells were administered several metal and near metal containing compounds, TGF-$\beta$ or selected bisphosphonate compounds. The metal and near metal compounds included ferric nitrate, ferric chloride, ferrous chloride, aluminum chloride, zinc chloride, gallium nitrate, cisplatin and spirogermanium. The metal and near metal compounds were tested at 50 $\mu$M. The selected bisphosphonates included EHDP and clodronate ($Cl_2MDP$) were administered at concentrations known to have antiresorptive activity. TGF-$\beta$ was tested at 5.0 ng/ml. The fibroblasts and osteoblasts were exposed to the compounds for 24–48 hrs., after which total cellular RNA was isolated by guanidinium isothiocyanate extraction and ultracentrifugation through cesium chloride. Chirgwin et al., "Isolation of Biologically Active Ribonucleic Acid from Sources Enriched in Ribonuclease", Biochem., 18:5294–5299 (1979). The RNA was separated by electrophoresis on a denaturing MOPS-formaldehyde agarose gel, (Biorad Products, Rockville Center, N.Y.) transferred to Nytran filters (Schleicher and Schuell, Keane, N.H.) and hybridized with [$^{32}$P]dCTP (New England Nuclear) labeled cDNA probes specific for the matrix proteins. The probes included: $\alpha_I(I)$ procollagen; osteocalcin; osteonectin; osteopontin; fibronectin; and constitutively synthesized proteins such as tubulin and $\alpha$-actin as controls. Radiolabeling of the probes was done according to the random priming method of Feinberg et al., "A Technique for Radiolabeling DNA Restriction Endonuclease Fragments to High Specific Activity", Anal. Biochem., 132:6–13 (1983). These probes were obtained from Drs.: David Rowe ($\alpha_I(I)$ procollagen, University of Connecticut, Storrs, Conn.); P. Robey (osteopontin, osteonectin, National Institutes of Health, Bethesda, Md.); John Wozney (osteocalcin, Genetics Institute, Cambridge Park, Mass.); R. Hynes (fibronectin, Rockefeller University, New York, N.Y.); and Lydia Pan ($\alpha$-actin, Stanford, Palo Alto, Calif.). Hybridization of the probes to the filters was performed according to the manufacturer's instructions. The hybridized filters (Northern blots) were washed under stringent conditions and exposed to X-ray film.

After developing the X-ray film, the bands corresponding to procollagen, fibronectin, osteopontin, osteocalcin and $\alpha$-actin mRNA's were scanned to provide an estimate of the percent change in mRNA levels after gallium nitrate treatment compared to control cells not treated with gallium nitrate. The X-ray films were scanned using an LKB Model 2202 Ultroscan Laser densitometer. The numbers shown in Table 1 represent the percent change compared to untreated cells.

The results, listed in Table 1, showed that only the gallium nitrate and TGF-$\beta$ caused an increase in $\alpha_I(I)$ procollagen, osteonectin and fibronectin mRNA with a concomitant decrease in osteocalcin. This result shows that only gallium nitrate mimics the changes seen when these same cells are exposed to TGF-$\beta$. Surprisingly, both ferric chloride and zinc chloride caused approximately two- to three-fold elevated levels of osteocalcin mRNA, an effect opposite to that of gallium or TGF-$\beta$.

TABLE 1

PERCENT CHANGE IN MATRIX PROTEIN mRNA LEVELS AFTER GALLIUM TREATMENT

| mRNA | Gallium Nitrate | TGF-$\beta$ | Zinc Chloride |
| --- | --- | --- | --- |
| OSTEOBLASTS | | | |
| $\alpha_1$ (I) Procollagen | +400 | +160 | — |
| Osteopontin | 0 | +70 | — |
| Osteocalcin | −40 | −40 | +270 |
| $\alpha$-Actin | +10 | — | — |
| FIBROBLASTS | | | |
| $\alpha_1$ (I) Procollagen | +400 | | |
| Fibronectin | +350 | | |

| mRNA | Ferric Chloride | Aluminum Chloride | EHDP or $Cl_2MDP$ |
| --- | --- | --- | --- |
| OSTEOBLASTS | | | |
| $\alpha_1$ (I) Procollagen | — | — | 0 |
| Osteopontin | — | — | — |
| Osteocalcin | +180 | 0 | 0 |
| $\alpha$-Actin | — | — | — |
| FIBROBLASTS | | | |
| $\alpha_1$ (I) Procollagen | | | |
| Fibronectin | | | |

Thus gallium nitrate, but not other metal- or near metal-containing compounds or bisphosphonates, increases the synthesis of mRNA encoding key stromal matrix components. There was no evidence for an increase in TGF-$\beta$ activity in the culture media of cells exposed to gallium nitrate, suggesting that the matrix enhancing effect was directly mediated by gallium nitrate, not indirectly through induction of TGF-$\beta$ synthesis. Additionally, several other metals appear to induce production of osteocalcin which would result in decreased matrix formation.

EXAMPLE 2

Gallium-Containing Compounds Enhance the de novo Synthesis of Collagen, a Key Structural Matrix Protein Example 1 showed that gallium nitrate specifically increased the expression of mRNA encoding structural matrix proteins in skin and bone-like cells. The experiment described below showed that the increased expression of bone matrix component mRNA is correlated with an increase in protein levels when healthy tissues were studied.

Calvarial (skull) bones from newborn rats were placed in sterile culture dishes with a nutritive media to maintain viability. In this state, structural tissues grow by forming new matrix components (notably bone-specific collagen), but this growth is very slow. Kream et al., "Characterization of the Effect of Insulin on Collagen Synthesis in Fetal Rat Bone", Endocrinol., 116:296–302 (1985). New bone-collagen synthesis was determined by measuring the uptake of [$^3$H]-proline or by following the appearance of [$^3$H]-hydroxyproline, which is formed by conversion of proline subsequent to its incorporation into collagen. Collagen is a unique protein, being almost entirely composed of proline, hydroxyproline, alanine and glycine.

Hemicalvaria from 21 day old fetal rats were incubated for 48 hours in the presence and absence of gallium nitrate at various concentrations as listed in Table 2. [$^3$H]-proline was added for the last 18 hours of the incubation.

The results obtained are presented in Table 2. The data are reported as counts per minute of [$^3$H] per mg bone (cpm/mg). With the addition of gallium nitrate at the therapeutic doses, (below 200 μM), a two-to-three fold enhancement in collagen synthesis, over controls, was measured.

TABLE 2

NEW COLLAGEN SYNTHESIS OF RAT CALVARIAL TISSUES

| Gallium nitrate concentration (μM) | Collagen Peptides (cpm/mg) | Hydroxyproline (cpm/mg) |
| --- | --- | --- |
| 0 | 14,486 | 1926 |
| 25 | 34,047 | 5886 |
| 50 | 36,734 | 6544 |
| 100 | 44,167 | 5426 |
| 200 | 12,104 | 1188 |

The data presented in Table 2 demonstrate that the increased collagen mRNA produced in osteoblasts exposed to gallium nitrate results in increased synthesis of the key matrix element collagen by connective and structural tissues. Similar effects were seen on collagen synthesis in bone cells exposed to TFG-β. Noda & Rodan, Ibid.

It is known that new collagen can be mineralized as evidenced by the increased uptake of [$^{45}$Ca] into newly formed bone matrix. Repo et al., "Effect of Gallium on Bone Mineral Properties", Calcif. Tissue Int., 43:300–306 (1988). Evidence of the ability of gallium-containing compounds to increase mineral matrix combined with the data presented above show that gallium-containing compounds enhance formation of both the mineral and organic matrices.

EXAMPLE 3

The Specific Decrease in Osteocalcin mRNA on Exposure to Gallium Nitrate is Associated With a Concomitant Decrease in Osteocalcin Protein Levels Osteocalcin is thought to slow or impede the formation of newly mineralizing bone. Therefore, a decrease in osteocalcin would be expected to benefit bone formation. Noda and Rodan, ibid. To determine if the decrease of osteocalcin mRNA noted on the exposure of cells to gallium nitrate (Example 1) was correlated with a concomitant decrease in osteocalcin protein levels, osteocalcin protein levels were measured in the culture media of the osteoblast cells after gallium nitrate treatment.

Osteocalcin levels were measured using a radioimmunoassay specific for osteocalcin. The radioimmunoassay was provided by Biomedical Technologies Inc., Stoughton, Mass. (BTI) and used according to the manufacturer's instructions. The levels of osteocalcin normally produced in osteoblast cells were compared to osteocalcin levels in identical cells exposed to gallium nitrate.

The results showed that the levels of osteocalcin fell from 1.3 to 0.63 nanograms per million cells after gallium treatment, confirming the correlation of a decrease in the production of osteocalcin with decreased levels of osteocalcin mRNA.

The decrease in osteocalcin levels induced by gallium nitrate is similar to the effects seen with the naturally occurring growth factor TGF-β normally found in bone and known to enhance matrix formation. No other metal or near metal is known to cause this effect on osteocalcin synthesis.

EXAMPLE 4

The Effect of Gallium Nitrate on in vivo Osteoblast Function

To determine the effect of gallium nitrate on osteoblast function in intact animals, an experimental model was used which reflects abnormal osteoblast activity. Gallium nitrate was analyzed for its ability to restore normal osteoblast activity to the experimental model.

The model for abnormal osteoblast activity was weanling Sprague-Dawley rats placed on a phosphate and vitamin D-deficient diet as per the manufacturer's instructions (the diet, #80039, Teklad, Madison, Wis.). The animals on the diet were also kept in the dark to prevent de novo vitamin D synthesis. Animals placed under such conditions show abnormal bone formation and a marked deficiency in total bone mass.

One group of the weanling rats on the diet was treated with gallium nitrate at 25 mg/kg, given as a subcutaneous injection, every other day for 21 days. One group on the diet remained untreated and served as the control. Littermate controls not on the diet and not treated with gallium nitrate supplied blood samples at the time of sacrifice of the animals on the diet for determination of alkaline phosphatase activity. Upon sacrifice, the long bones were removed from the animals on the diet for subsequent analyses.

As previously noted, serum alkaline phosphatase activity is used as a reliable indicator of osteoblast activity, such that increased levels of alkaline phosphatase activity are evidence of the abnormal bone turnover in the experimental animals. Serum alkaline phosphatase activity was determined by measuring the hydrolysis of p-nitrophenyl phosphate by serum samples according to the method of Lowry et al., "Histochemistry of Brain", J Biol Chem., 207:19–37 (1954).

The results showed that serum alkaline phosphatase activity was markedly elevated in the animals on the diet that were not treated with gallium nitrate; 660±20 units/ml vs 470±40 units/ml for littermate controls not on the diet. By contrast, the animals on the diet treated with gallium nitrate show normalization of bone cell function as evidenced by the lower level of serum alkaline phosphate activity; 250±30 units/ml. Further, the gallium nitrate treated animals showed greater bone mass, examination of the ash weights of bones from the animals on the diet showed there was a significant increase (2% ± 0.5%) in bone mineral in the gallium-treated rats compared to the untreated rats. These results indicate enhanced matrix synthesis during gallium treatment in the intact animal.

The results obtained from this experiment indicate that in this rat model system treatment with a therapeutically active formulation of gallium resulted in a normalization of osteoblast cell function with an attendant increase in bone mass.

The terms and expressions employed herein are used as terms of description and not of limitation, and there is no intention in the use of such terms and expressions of excluding any equivalents of the features shown and described or portions thereof, it being recognized that various modifications are possible within the scope of the invention.

EXAMPLE 5

Gallium Effect on Human Keratinocyte Proliferation

A critical step in wound healing of skin tears and breaks is the re-epithelization of the wound. An initial step in wound healing is the proliferation of specific skin cells known as keratinocytes. These cells grow into a wound from the edges to provide a protective cellular barrier over the wound. At the present time, the endogenous natural growth factors in skin that can initiate this critical proliferation have not been fully identified. When freshly isolated human keratinocytes were treated with gallium nitrate, low concentrations of gallium induced a proliferative response.

Human keratinocytes were prepared from split thickness skin specimens removed from cadavers, as previously described, Staino-Coico et al., "Human Keratinocyte Culture", J. Clin. Invest., 77:396–404 (1986). Briefly, the tissue specimens were suspended in sterile Eagle's minimum essential medium containing antibiotics to prevent bacterial and fungal growth. The tissue was placed in phosphate-buffered saline that contained 0.5% trypsin but was calcium and magnesium free, for 90 minutes at 37° C. Single cell suspensions were prepared by the addition of 0.25% DNase I, then fetal calf serum followed by filtration through sterile gauze. The isolated cells were harvested by centrifugation then resuspended in media containing 20% fetal bovine serum supplemented with amino acids, hormones and antibiotics. All reagents and media were obtained from Sigma Chemical Company, St. Louis, Mo.

By measuring keratinocyte cell numbers, it was shown that a 10 µM concentration was sufficient to produce a doubling in keratinocyte cell number after seven days. The results are shown in Table 3 where the cell count is in the millions and the control is untreated cells.

TABLE 3

| Effect of Gallium on Human Keratinocytes | | |
|---|---|---|
| Day of Study | Control | Gallium |
| 3 | 3.12 ± 0.58 | 3.45 ± 0.40 |
| 7 | 2.80 ± 0.81 | 5.33 ± 0.15 |

Increasing keratinocyte proliferation means that wound healing is accelerated. The protective barrier over the skin wound is thus established earlier allowing subsequent healing to proceed in a protected and sterile environment. Wound infection due to inadequate sealing of the wound is probably one of the major impediments to wound healing. Coupled with known enhancement of fibroblast production of key matrix components, gallium-containing compound treatment of skin wounds greatly facilitates and accelerates wound healing.

We claim:

1. A method of enhancing connective and support tissue repair and augmentation, wherein the tissue is selected from the group consisting of skin, tendon, fascia, and collagen-containing tissues that encapsulate organs, comprising administering an amount of a pharmaceutically acceptable gallium-containing compound which is effective for enhancing connective and support tissue repair and augmentation and providing therapeutic levels of elemental gallium.

2. The method according to claim 1 wherein the gallium-containing compound is selected from the group consisting of gallium nitrate, gallium citrate, gallium phosphate, gallium chloride, gallium fluoride, gallium carbonate, gallium acetate, gallium tartrate, gallium maltol, gallium oxalate, gallium formate, gallium oxide, hydrated gallium oxide and coordination complexes of gallium and protein bound gallium.

3. The method according to claim 2 wherein the coordination complexes of gallium are selected from the group consisting of gallium pyrones, gallium pyridones, gallium hydroxymates, gallium aminocarboxylates and gallium oximes; and the protein to which gallium is bound is selected from the group consisting of transferrin and lactoferrin.

4. The method according to claim 1 wherein the gallium-containing compound is administered via a route selected from the group consisting of topical, transdermal, parenteral, intraarticular, gastrointestinal, transbronchial and transalveolar.

5. The method according to claim 1 wherein the gallium-containing compound is administered proximate to the site of injury in an amount sufficient to attain local tissue levels of 0.25–100 µM elemental gallium.

6. The method according to claim 1 wherein the gallium-containing compound is administered in an amount sufficient to maintain steady state tissue levels of about 1.0 to 1000 ng elemental gallium per mg dry weight of tissue.

7. The method according to claim 1 wherein the gallium-containing compound is administered in an amount sufficient to maintain steady state tissue levels of about 1.0 to 500 ng elemental gallium per mg dry weight of tissue.

8. The method according to claim 1 wherein the gallium-containing compound is administered in an amount sufficient to maintain steady state blood concentrations of about 1–150 µM elemental gallium.

9. The method according to claim 1 wherein the gallium-containing compound is administered in an amount sufficient to maintain steady state blood concentrations of about 1–50 µM elemental gallium.

10. A method of enhancing repair and augmentation of the skin comprising administering an amount of a pharmaceutically acceptable gallium-containing compound effective in providing a local concentration of elemental gallium of between 0.25 and 100 micromolar.

* * * * *

UNITED STATES PATENT AND TRADEMARK OFFICE
CERTIFICATE OF CORRECTION

PATENT NO. : 5,556,645

DATED : September 17, 1996

INVENTOR(S) : Bockman et al.

It is certified that error appears in the above-indentified patent and that said Letters Patent is hereby corrected as shown below:

Title page, Item 56, 10th line, "Ribunocleic" should read --Ribonucleic--;

Title page, Item 56, bridging lines 10-11 "Ribunoclease" should read --Ribonuclease--;

Title page, Item 56, line 17, "Bogelstein" should read --Vogelstein--;

Title page, 1st col., 5th-from-bottom line, "Ebdocrin" should read --Endocrin--;

Title page, 2nd col., 1st line, "Brian" should read --Brain--;

Title page, 2nd col., 4th line, "Osteosarcoma,a" should read --Osteosarcoma,--;

Title page, 2nd col., 6th line, "Typeβ" should read --Type β--;

Title page, 2nd col., 7th line, "Espression" should read --Expression--;

Title page, 2nd col., 11th line, "Mineral" should read --Bone Mineral--;

Title page, 2nd col., 13th line, "Robery" should read --Roby" AND "Respind" should read --Respond--;

Title page, 2nd col., last line of Item 56, "261:5693±145" should read --261:5693-5695--;

Page 2, 1st col., 3rd line, "Diposphonate" should read --Diphosphonate--;

UNITED STATES PATENT AND TRADEMARK OFFICE
CERTIFICATE OF CORRECTION

PATENT NO. : 5,556,645

DATED : September 17, 1996

INVENTOR(S) : Bockman et al.

It is certified that error appears in the above-indentified patent and that said Letters Patent is hereby corrected as shown below:

Col. 2, line 34, "animmune" should read --an immune--;

Col. 4, line 41, "explain" should read --and explain--;

Col. 8, line 4, "De" should read --be--;

Col. 10, lines 56-57, "no figures appearing alongside the two items listed"

Signed and Sealed this

Twenty-fifth Day of February, 1997

Attest:

BRUCE LEHMAN

Attesting Officer

Commissioner of Patents and Trademarks